United States Patent [19]  [11] 4,331,151
Golden  [45] May 25, 1982

[54] HEMORRHOID BANDAGE
[76] Inventor: Theodore A. Golden, 755 W. Big Beaver Rd., Troy, Mich. 48084
[21] Appl. No.: 185,259
[22] Filed: Sep. 8, 1980
[51] Int. Cl.³ ......................... A61F 7/12; A61B 17/36
[52] U.S. Cl. .............................. 128/401; 128/303.12; 128/400
[58] Field of Search .............. 128/341, 343, 400, 401, 128/303.12

[56] References Cited
U.S. PATENT DOCUMENTS

| | | | |
|---|---|---|---|
| 601,345 | 3/1898 | Korb | 128/343 |
| 2,024,301 | 12/1935 | Norwood | 128/344 |
| 2,548,602 | 4/1951 | Greenburg | 128/344 |

Primary Examiner—Robert W. Michell
Assistant Examiner—C. W. Shedd
Attorney, Agent, or Firm—Cullen, Sloman, Cantor, Grauer, Scott & Rutherford

[57] ABSTRACT

A hemorrhoid bandage or cold pack, for positioning within a human anal canal, is formed of a hollow, thin wall, roughly cylindrically shaped body having an inner end and an outer end. The body is transversely divided into two parts by a central panel extending longitudinally from the outer end towards the inner end, but having an open area adjacent the inner end. A tube, which is coaxial with the body, extends from the inner to the outer end and opens exteriorly of the body at each end. A fluid inlet continuously supplies fluid of a predetermined temperature into one body part through the outer end, which fluid flows through the panel open area at the inner end, and then out of the other body part through a fluid drain opening communicating therewith. The two interior parts may be further subdivided by transverse ribs extending between the panel and the body exterior wall to form longitudinally extending channels for controlling the direction of the fluid flow through the body. By using a relatively cool fluid, such as cool water, the bandage may be used to provide a controlled temperature, for extended periods of time, within the rectal area in connection with treatment of hemorrhoids.

5 Claims, 6 Drawing Figures

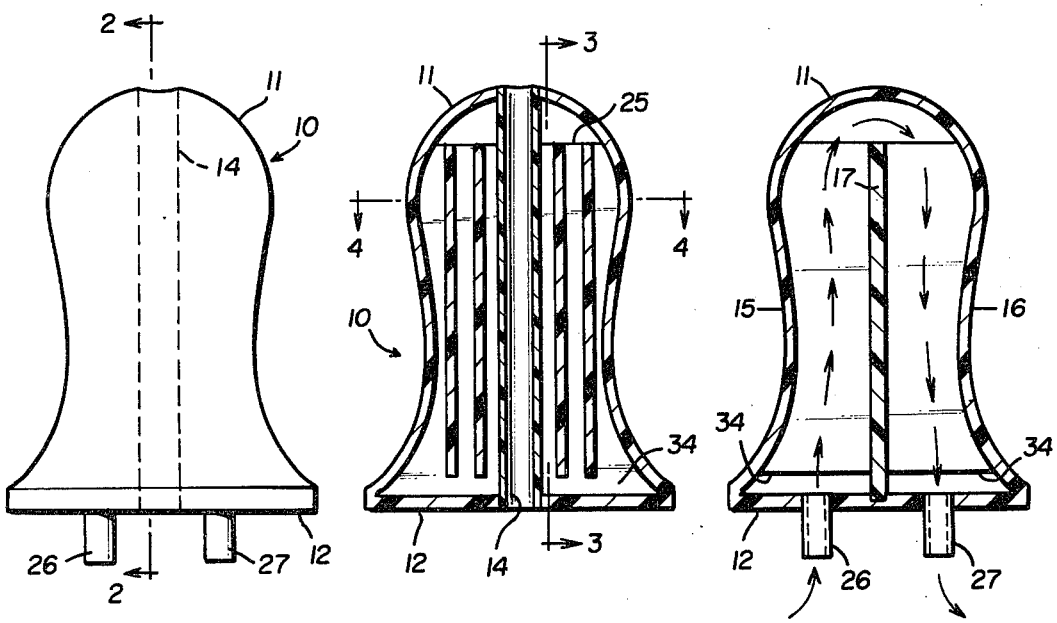
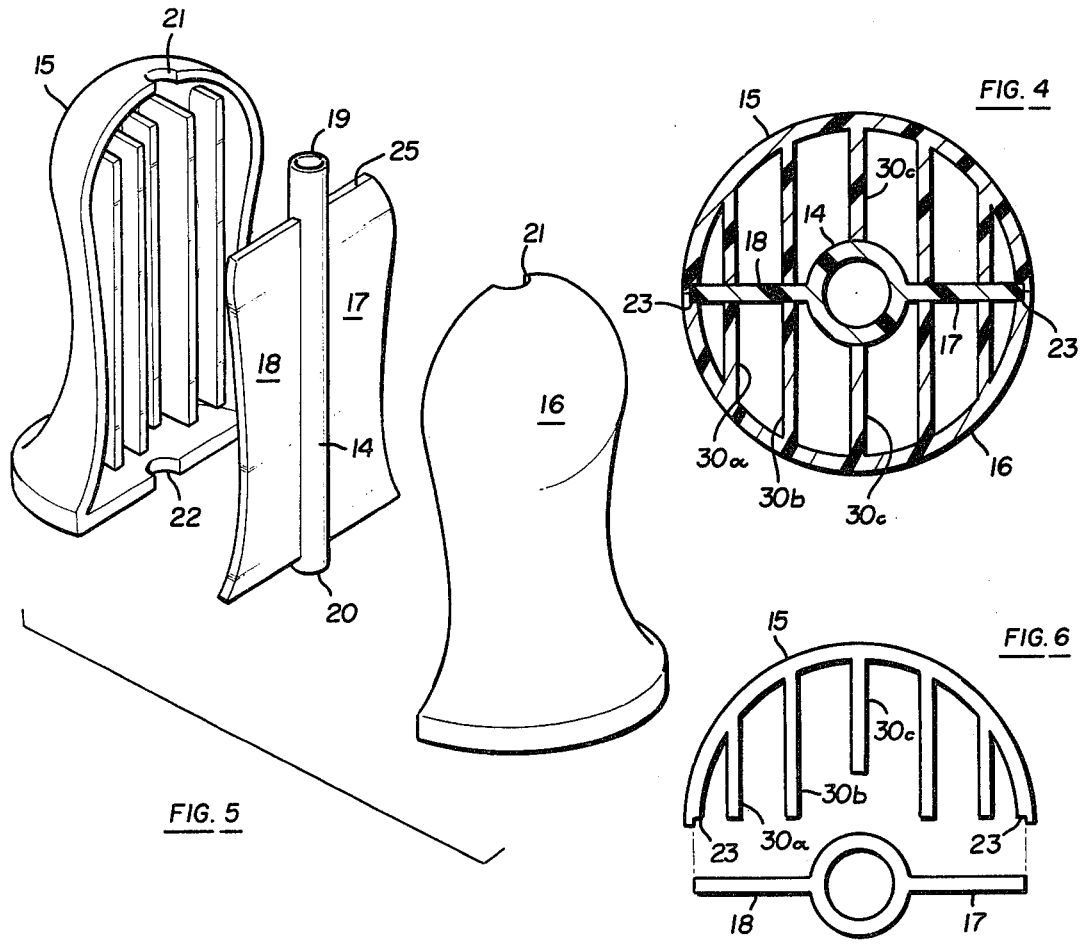

HEMORRHOID BANDAGE

BACKGROUND OF THE INVENTION

The invention herein relates to a thermally controlled bandage or pack useful for providing a controlled temperature within the human anus or rectal area for either post operative treatment or other care or treatment of hemorrhoid conditions. The device is useful for maintaining a predetermined cool temperature within the treated area for extended periods of time without interfering with the expulsion of the human body gases and body fluids.

Thermally controllable bandages or packs for application to exterior surfaces of the human body are disclosed in my prior U.S. Pat. No. 4,098,279 issued July 4, 1978 for a therapeutic thermal pack unit and in my prior U.S. Pat. No. 4,108,146 issued Aug. 22, 1978 for a bendable thermal pack unit. Each of these prior patented devices contemplate bandages or packs which are hollow and made of thin material. Thermally controlled fluid, such as cool water at a predetermined temperature is flowed through the pack. Consequently, the exterior surfaces of the pack are maintained at a steady cool temperature for long periods of time so that the human body portion covered by the pack is cooled, generally for post operative care to control swelling, bleeding, and the like.

With this type of thermal pack, the temperature can be controlled to the point where it is comfortable or if not comfortable, at least acceptable, to the user as contrasted with ice packs and other cold packs which are usable only for short periods of time before exceeding the limits of comfort and tolerance of the user.

Prior to the invention herein, there has been no comparable thermally controlled pack or bandage useful for the human rectal or anus areas. Yet, it is desirable to apply a uniform cooling temperature within those areas for certain hemorrhoid treatment purposes, particularly for post operative care or for other comparable treatments. The common use of so called sitz-baths, involving the patient sitting within a tub of water of predetermined temperature, while useful for many purposes, is limted because of the inconvenience and discomfort over a long period of time. Moreover, temperature control over an open vessel or tub of water is not practical so that uniformity of temperature is normally not available. Consequently, the invention herein contemplates the provision of thermal pack or bandage useful in a body orifice, particularly the anus for use in handling or treating hemorrhoid conditions.

SUMMARY OF INVENTION

The invention herein contemplates providing an elongated roughly cylindrically shaped, or more accurately an elongated bell-shaped, thin wall plug-like body having closed inner and outer ends for insertion in the anus. Preferably, the body is pliable or flexible for comfort and ease of insertion and removal.

The body includes a tube extending from one end to the other through which human body fluids and gases may be expelled while the plug is arranged within the anus or other like body cavity.

The pack is divided, by a panel extending transversely thereof, into opposing parts. Fluid is flowed into one part, around the inner end of the panel and outwardly through the other part and then outwardly of the pack through a drain opening. Thus, fluid, such as cool water of a predetermined temperature, may be constantly flowed through the pack for extended periods of time for maintaining the temperature of the pack at a predetermined, tolerable degree.

In addition, it is contemplated to provide transversely extending ribs or fins within the body which are integral with the body walls and joined to either the central tube or the panel or both. These ribs from divided channels extending longitudinally, i.e., from the outer end to the inner end of the bandage, for better directing the flow of the fluid and maintaining a more uniform temperature. Further, the arrangement of the ribs and panel and tube provides an internal stiffening wherein the thin, membrane-like wall of the pack will maintain its complex contour under the internal pressure of the fluid as well as under the external pressure of the human body contacted portions.

One object of this invention is to provide a simple plug-like bandage or pack which may be easily inserted into the human rectal area and maintained therein for long period of time, with relative comfort, to maintain a predetermined temperature therein, thereby providing thermal treatment which has not previously been available in hemorrhoid cases except through the use of sitz-baths and the like which are not as convenient, comfortable, or useable for long periods of time.

Another object of this invention is to form a plug-like pack or bandage for hemorrhoid condition thermal treatment, which is relatively simple in construction, light weight and easy to handle and operate and useable for long periods of time.

Yet a further object of this invention is to provide a thermal pack or plug for insertion within the human rectal area which will provide a uniform, predetermined temperature over a long period of time without attention or human control during that period of time so the device may be easily used by a patient who is substantially unattended.

Further objects and advantages of this invention will become apparent upon reading the following description, of which the attached drawings form a part.

DESCRIPTION OF DRAWINGS

FIG. 1 illustrates an elevational view of the hemorrhoid bandage or thermal pack of this invention.

FIG. 2 is a cross sectional view of the thermal pack taken in the direction of arrows 2—2 of FIG. 1.

FIG. 3 is a cross sectional view of a segment of a pack taken in the direction of arrows 3—3 of FIG. 2.

FIG. 4 is a greatly enlarged cross sectional view taken in the direction of arrows 4—4 of FIG. 2.

FIG. 5 is a disassembled view of the parts forming the bandage.

FIG. 6 is an enlarged, cross sectional view, of one of the bandage body halves or shells with the tube-panel unit disassembled.

As illustrated in FIG. 1, the hemorrhoid bandage or thermal pack 10 is formed in an elongated, generally cylindrical shape. Preferably the pack varies somewhat in diameter, from one end to the other, so that it may more nearly approximate a roughly elongated bell-like shape with a closed and rounded inner end 11 and a flat, closed outer end 12. Inner and outer refers to the interior of the human body or the exterior of the body, i.e., the direction in which the plug-like thermal pack or bandage is inserted in the human anus.

A central tube 14 extends from one end of the body to the other and opens exteriorly thereof. This tube permits the passage of the human body gases and fluids during the time of insertion of the plug-like pack within the orifice.

Preferably, the body of the bandage or pack is made of a pair of opposed, mirror image, halves or shells 15 and 16. Between the shells is positioned a panel formed of a pair of plates 17 and 18 which are integral with the central tube 14 and extend diametrically opposite of each other in a common plane.

The central tube has an upper tube extension 19 which extends above the panel and a lower tube extension 20 which extends below the panel, with the extensions fitted within registered upper openings 21 and registered lower openings 22 in the pair of shells.

The free edges of the plates fit within notches or rabbit 23 formed in the adjacent or abutting ends of the shells. Thus, the free edges of the plates and the shells are arranged together and secured together with a suitable adhesive bonding or thermal bonding.

The upper end 25 of the panel, i.e., both plates 17 and 18, are spaced a distance outwardly of the inner end 11 of the bandage to form a space which communicates the interior of one shell with the interior of the opposite shell.

An inlet tube 26 is secured within an opening formed in the outer end 12 of one shell and an outlet tube 27 is secured within the outer end of the opposite shell. Thus, fluid, such as cool water, may be constantly pumped, using a suitable pumping and cooling mechanism, through the inlet tube 26 into one part of the body and then inwardly towards the inner end of the body. Thereafter, the water or fluid flows through this space between the inner end 25 of the panel and the interior wall surface of the inner end of the body, into the opposite bandage body part and then out through the outlet tube 27. This provides a constant flow path for the fluid.

In order to better direct the cooling fluid, each of the shells 15 and 16 is provided with a number of thin ribs 30a, 30b, 30c and opposite ribs of the same configuration and length. These ribs separate the shell or body half into a number or parallel channels so that the fluid is directed through the channels for better cooling of the thin walls of the body.

The outer ends of the ribs are spaced inwardly of the outer end wall 12 to provide a space or manifold 34 which functions as a common header for distribution of the fluid or collection of fluid, as the case may be.

Although the specific sizes and shape of the bandage of or plug may vary, by way of example, a typical plug or bandage of roughly three inches in length would be suitable for most uses. The largest diameters, which appear near the inner end and also at the outer end 12, may be on the order of roughly two inches. The narrowest diameter, which appears between the opposite ends, but nearer to the outer end, may be on the order of roughly one-half to one inch. The wall thicknesses may be roughly 0.025 inches and the ribs may be somewhere in the neighborhood of 0.100 thick with a 0.200 space between the ribs. One material found suitable for this construction is a so-called medical polyvinyl material which is commercially available, although the specific material may be varied depending upon availability and the technique used for forming the body parts.

The interior tube 14 may have a tube wall thickness comparable to the wall thickness of the body, with a tube internal diameter of roughly 0.25 inches to give adequate passageway through the plug-like pack.

Moreover, the plug or body may be formed, instead of two halves or opposing shells, as a single, elongated central unit with separate inner and outer ends adhesively secured thereto. Likewise, the ribs, instead of being parallel, may in some instances, depending upon cost and strength requirements, be arranged on a radial pattern, i.e., extending between the interior tube and the interior wall of the body. The separate parts are adhered together by a suitable commercially available adhesive, of which there are a number available, or alternatively, by appropriate heat sealing or bonding.

If the material forming the wall of the bandage is sufficiently stiff, the interior ribs may be eliminated or the number lessened. However, where the material used is thin and pliable and membrane-like, the ribs function to maintain the complex shape of the plug-like body despite the considerable interior pressure of the fluid and the considerable exterior pressure applied by the human body.

The bandage may be appropriately sized to fit body orifices or cavities other than the anal canal, as for example, the vaginal canal, or ears or nostrils, as may be medically desirable.

In operation, the patient, or an attendant may easily insert the bandage or pack within the orifice and connect to the inlet and outlet tubes lengths of suitable rubber-like tubing. Such tubing may be connected to a pumping mechanism for pumping water at a predetermined temperature and for receiving the water flowed from the bandage. Because the temperature can be regulated at any particular degree desired, the body portions may be cooled without overly chilling them so that the device may be used, with relative comfort, over a long period of time to alleviate some of the pain, such as that caused by hemorrhoid treatment or by surgery, or to provide the cooling effect desired in treating hemorrhoids or other cavity ailments.

Having fully described an operative embodiment of this invention, I now claim:

1. A thermally controllable bandage comprising an elongated, hollow interior, thin wall, generally cylindrically shaped body having a first end and a second end, and being of a size for positioning within a human body cavity with the second end exposed at an open end of the cavity;

a tube extending through the length of the body and opening exteriorly of said bandage body at both ends of the bandage body;

a fluid inlet and a fluid outlet each formed at the body second end for flowing fluid of predetermined temperature into the hollow interior of the body and for removal of the fluid from the body interior;

a thin panel formed inside the hollow interior of the body and extending transversely thereof from side-to-side of the body to the tube, so that the panel together with the tube form a wall for dividing the interior of the body into separate parts;

said panel formed of a pair of coplanar thin, flat plates formed integral with a portion of said tube and extending diametrically outwardly of said tube so that the tube and panel form a single unit interiorly of said hollow body said tube extending beyond the ends of said panel;

said panel and tube dividing said body longitudinally, from said first end to said second end, into two opposed mirror image halves, each generally shaped as a hollow bell-like elongated generally cylindrical form, with the free edges of each half abutting and secured together to form the complete hollow body;

the free edges of the plates being fastened to said body halves along the line of securement of the body halves to each other so that the two body halves and the single unit tube and panel may be simultaneously joined together at their adjacent abutting edges;

said fluid inlet and fluid outlet each communicating with a separate interior part so that fluid may be continuously flowed into one of said separate parts and continuously drained from the other part; and said panel ends terminating a distance inwardly of said body first end so that fluid can flow between said separate interior parts;

wherein the body may provide a predetermined, controlled temperature for extended periods of time and gases and fluids of the human body may be expelled through the tube.

2. A bandage as defined in claim 1, and including a number of spaced apart ribs located within the hollow interior of the body that extend from each side wall portion of the body transversely toward said panel and being of a length extending from the first end of the body toward the second end thereof, to form each separate part of the body, i.e., on the opposite sides of the panel, into spaced channels divided by the ribs, with a header portion formed within each body part for communicating with all the channels in that part;

and said fluid inlet and fluid outlet each communicating with one of said header portions;

whereby fluid may be continuously directed from the header portion communicating with the fluid inlet through the channels in that part of the body, through the area between the panel ends and the first end of said body, into the channels in the other part and out the header portion communicating with the fluid outlet for the other part, for fluid circulation through the bandage.

3. A bandage as defined in claim 1, and said body being of varying cross-sectional diameter which is wider at its second end and also near its first end and narrowest at generally the middle of its length, with the diameter gradually increasing between the narrow and the wider portions to form an elongated bell-like exterior configuration.

4. A bandage as defined in claim 3, and with the walls of said body being relatively thin and of approximately uniform thickness throughout the body for substantially uniformly cooling the surface of the body by means of the continuous flow of the fluid through the body.

5. A bandage as defined in claim 1, and with the walls defining said body being formed of a pliable, thin material of uniform thickness;

and the body shape varying in cross sectional diameter from the first end to the second end in a, generally elongated bell-like shape;

and including a number of spaced apart ribs located within the hollow interior of the body, each formed integral with the inner wall surface of the body and extending toward said panel and joined thereto, with the ribs defining spaced channels between them and including a first common header portion between the fluid inlet and the end of each of the channels adjacent the body second end in the first body part, and a second common header portion between the fluid outlet and the end of each of the channels adjacent the body second end in the other body part;

said ribs being likewise of thin, pliable material;

whereby the rib and panel arrangement holds the complex contoured shape of the body under fluid pressure so that the body substantially maintains its shape despite internal pressure caused by the fluid flowing interiorly of said body and despite the external pressure applied by the human body within which the bandage is inserted.

* * * * *